(12) United States Patent
Kelman et al.

(10) Patent No.: US 6,527,765 B2
(45) Date of Patent: Mar. 4, 2003

(54) CRYOGENIC SURGICAL SYSTEM AND METHOD OF USE IN REMOVAL OF TISSUE

(76) Inventors: Charles D. Kelman, 721 Fifth Ave., Apt. 58L, New York, NY (US) 10022; Roman Perez-Soler, 87 Old Field Rd., Setauket, NY (US) 11733

(*) Notice: Subject to any disclaimer, the term of this patent is extended or adjusted under 35 U.S.C. 154(b) by 0 days.

(21) Appl. No.: 09/773,986

(22) Filed: Feb. 1, 2001

(65) Prior Publication Data

US 2002/0042609 A1 Apr. 11, 2002

Related U.S. Application Data

(63) Continuation-in-part of application No. 09/684,544, filed on Oct. 6, 2000.

(51) Int. Cl.[7] .......................... A61B 17/22; A61B 19/00
(52) U.S. Cl. ..................... 606/22; 606/107; 606/169; 606/171; 604/22; 604/35; 128/898
(58) Field of Search .................. 606/22–26, 107, 606/169, 167, 171; 604/22, 27, 35; 128/898

(56) References Cited

U.S. PATENT DOCUMENTS

| | | | | |
|---|---|---|---|---|
| 3,809,093 A | * | 5/1974 | Abraham ................ 606/169 |
| 3,942,519 A | * | 3/1976 | Shock .................... 606/169 |
| 5,989,209 A | * | 11/1999 | Barrett .................... 604/22 |
| 6,032,675 A | * | 3/2000 | Rubinsky ................ 128/898 |

* cited by examiner

*Primary Examiner*—David M. Shay
(74) *Attorney, Agent, or Firm*—Darby & Darby

(57) ABSTRACT

The present invention is directed towards a surgical system and method of use for treating and removing unwanted tissue, preferably from an organ or other internal part of a patient. The system includes a cryosurgical component for first freezing the unwanted living tissue by forming an ice mass which completely encompasses the unwanted living tissue and means for treating the cryogenically-treated tissue and then removing the tissue while it remains in a frozen state. In one embodiment, an ultrasonic device is used to ultrasonically vibrate the cryogenically-treated tissue to break apart the frozen tissue and the frozen broken-up pieces of tissue are removed using a technique, such as an aspiration process.

37 Claims, 4 Drawing Sheets

CRYOGENIC SURGICAL SYSTEM AND METHOD OF USE IN REMOVAL OF TISSUE

CROSS REFERENCE TO RELATED APPLICATIONS

The present application is a continuation-in-part application of co-pending U.S. application Ser. No. 09/684,544, filed Oct. 6, 2000, and which is herein incorporated by reference in its entirety.

FIELD OF THE INVENTION

The present invention relates, generally, to a system and method for treating and removing tissue and, more particularly, to a system and method of use which includes a cryosurgical instrument for isolating and freezing unwanted living tissue and means for vibrating or otherwise treating the cryogenically-treated tissue and removing the tissue.

BACKGROUND OF THE INVENTION

In many types of medical procedures, tissue specimens of a patient are removed either for diagnostic purposes to study the tissue or for treatment purposes. For example and quite frequently, these tissue specimens include a cancerous tumor or other unwanted localized growth which is then preferably entirely excised from the patient during the medical procedure.

It is important that the cancerous tumor or other growth is localized and entirely removed from the patient to reduce or eliminate the risk that the tumor will return over time and/or will spread to other parts of the body. Therefore, in order to ensure that the tissue associated with the tumor is completely removed, the exterior of the removed section is carefully microscopically studied in order to determine whether there is only good healthy tissue or whether unwanted tissue is present. A physician can thus determine if a portion of the tumor has been left within the good healthy tissue. If this occurs, the physician removes another deeper layer of the good tissue and again performs the procedure.

However, one of the associated risks of removing cancerous tumors is that during one or more of the medical procedures, a portion of the cancerous tumor may separate and spread to another part of the patient's body. This may result in further medical complications including the risk that the cancer may spread to another part of the patient's body. It is therefore important that great care and precision be taken in removing the cancerous tissue (tumor).

Typically, the surgical approach for removing the cancerous tissue has involved open surgical procedures. However, such procedures may be accompanied by surgical trauma, such as formation of scar tissue, lengthy recuperation and pain and therefore there has been an increasing desire to expand the use of microsurgical techniques. These microsurgical techniques require the use of highly specialized instruments and therefore are generally much more intricate, time-consuming, and stressful than open surgical procedures. However, the use of microsurgical techniques does greatly reduce some of the common surgical traumas associated with open surgical procedures.

Over the past years, cryosurgical procedures have been advanced and more applications are being discussed for such surgical procedures. Cryosurgery is a surgical procedure that uses freezing temperatures to destroy tissue. Until recently, cryosurgery was utilized almost entirely for the treatment of tumors on the outer surface of the body, such as for treatment of skin cancer. Generally, in cryosurgical procedures, the tumor or the like is frozen to a temperature of preferably about $-50°$ C. in order to attempt to completely destroy all of the cells of the tumor. After treating the cells of the tumor, the tumor is typically left in the body for the body to absorb. Thus, the tumor is not removed but rather remains in the body as the extent of the cryosurgical procedure is to simply freeze the cells to a point which hopefully causes the destruction of the cells.

One of the associated disadvantages is that it is difficult, if not impossible, to observe the extent of the frozen region using more conventional cryosurgical instruments. Thus, the difficulty with performing a cryosurgical procedure is that it is not easy to determine whether all of the cells, associated with the nondesirable tissue, have been destroyed. This is especially true when the surgeon simply tries to cryogenically treat only the nondesirable tissue itself. Cryosurgery is therefore a rather imprecise procedure and it is difficult to control the actual cryogenic freezing and destroying of all of the cells associated with the nondesirable tissue. For example, it is difficult to control the freezing gradient and rate of freezing when using cryosurgical instruments. It is also very difficult to predict or determine how many cells of the nondesirable tissue are destroyed during the cryosurgical procedure. As one of skill in the art will appreciate, it is of great importance that all of the cells associated with the nondesirable tissue are destroyed because the existence of even a few of these cells can cause regrowth of the nondesirable tissue and also provides an opportunity for the cells to travel to other locations of the body. Because the treated tissue is left in the body for absorption, any cells which are not destroyed remain in the body and can spread to other locations.

Advances in monitoring and imaging techniques have expanded the potential applications for cryosurgical procedures and have permitted this type of procedure to treat tissue deep within the body, e.g., organ or gland tissue. Monitoring by imaging techniques, such as magnetic resonance imaging or ultrasound, can be used to intraoperatively determine, in real time, the extent of the tumors as well as that of the frozen tissue during cryosurgery. Ultrasound techniques work by sensing a pressure wave from a pressure transducer. The wave is reflected from boundaries between regions that have differences in acoustic impedance such as between tumors and normal tissue, blood vessels and tissue and frozen and unfrozen tissue. The reflected wave is identified by the pressure transducer and the extent of the tumor, or of the frozen region, is shown on a monitor. Following computerized interpretation of the data, this procedure facilitates an accurate identification of the extent of the tumor and of the frozen region during the cryosurgery.

In addition, there is now a better understanding of the process by which a cell freezes and is destroyed. It is believed that freezing in tissue is greatly influenced by the structure of the tissue. The destruction of the frozen tissue is promoted by the fact that during freezing the vasculature network of the tissue is destroyed and, therefore, cancerous and other nondesirable cells in the region that has been frozen are deprived of their blood supply after thawing and die because of ischemic necrosis. The destruction of frozen tissue also results because ice spicules that are formed during the freezing process rupture the cell membranes and therefore cause the destruction of these cells.

It is therefore desirable to provide a surgical system and method for treating and removing cancerous or other nondesirable tissue from deep within a patient's body, e.g., within an organ or gland, wherein the system is simple yet effective and eliminates or substantially reduces the risk that cancerous cells might spread to other locations and also overcomes the disadvantages associated with the more conventional procedures.

SUMMARY OF THE INVENTION

The present invention provides a surgical system and method of use for treating and removing unwanted tissue, such as a cancerous tumor or other growth, which is formed within a patient's body, e.g., within an organ, gland, or other internal part of the body. The present system is simple yet effective to use and provides a relatively minimally-invasive surgical approach to treating and removing such unwanted tissue.

In one embodiment, a single probe type instrument is used to carry out the surgical procedure of the present invention. The instrument includes a delivery system for delivering a cryogenic fluid to a tip portion of the instrument so that the unwanted tissue is frozen by being placed in contact with the cryogenically-cooled tip portion. The instrument also includes means for vibrating the tip portion to cause the disintegration and break-up of the cryogenically-treated tissue. Preferably, the tip portion is vibrated at frequencies to cause the frozen tissue to disintegrate and break apart. The disintegrated, frozen broken-up pieces or frozen granules of tissue are preferably suspended in a super cooled irrigation fluid which is introduced to the operative site using the instrument. A suction component of the instrument then aspirates the super cooled irrigation fluid and broken-up pieces of the frozen tissue from the operative site. It will be appreciated that other types of devices may be used to disintegrate and break apart the tissue. For example, an impacting device with a rotatable tip may be incorporated into the single probe type instrument instead of a vibrating tip.

More specifically and in accordance with one aspect of the present invention, an ice mass, e.g., an ice sphere, forms during the cryosurgery and completely encompasses the unwanted tissue so that all of the unwanted tissue is maintained at a temperature below freezing. The ice mass forms because individual cells are formed largely of water and thus exposure to temperatures below their freezing point causes the cells to freeze and expand. When a number of surrounding tissue cells freeze and expand, they collectively form the ice mass. The formation of the ice mass serves to isolate the unwanted tissue by encompassing it within the ice mass and importantly makes sure that all of the cells of the unwanted tissue are continuously maintained in a frozen state. By preferably encompassing the unwanted tissue within the ice mass, the frozen unwanted tissue may easily be removed. In other words and according to the present invention, the unwanted tissue is removed while in a frozen state. The complete removal of the unwanted tissue, while it remains in a frozen state, eliminates the risk that any cells of the unwanted tissue remain within the body.

In another embodiment, two or more surgical instruments are used. A system according to this embodiment generally includes a cryosurgical instrument, including a cryoprobe, for cryogenically-treating the unwanted tissue. Within the cryoprobe, a liquid refrigerant (e.g., nitrogen oxide) is circulated so that a probe tip reaches and maintains a temperature below the freezing point of tissue and preferably below about −50° C. An incision is made in the skin layer and the probe tip is inserted therethrough so that the probe tip is brought into contact with the unwanted tissue. This contact at these low temperatures causes necrosis to occur in the cells of the unwanted tissue and this results in the freezing of these cells. In addition, ice spicules form during the freezing process and these ice spicules rupture surrounding cell membranes, thereby resulting in the formation of the ice mass.

The cryosurgical instrument thus serves to freeze and isolate the unwanted tissue by encompassing it within the ice mass prior to the tissue being further prepared and then removed according to techniques of the present invention. Suitable monitoring devices, which permit imaging of the operative site, may be used so that the surgeon can determine, in real time, the extent of the unwanted tissue as well as the extent of the frozen tissue. Preferably, the location of the unwanted tissue is first determined using a catscan device, fluoroscope, etc.

After the unwanted tissue has been cryogenically frozen, the tissue is then further prepared and finally removed using one or more surgical instruments. In one embodiment, a vibrating instrument (e.g., sonic or ultrasonic instrument) is used to disintegrate and break apart the frozen tissue to facilitate the removal thereof. In other words, the instrument disintegrates and loosens the frozen tissue which forms the ice mass while still in the frozen state. A tip portion of the instrument is brought into contact with the ice mass and the tip portion is manipulated so that the ice mass surfaces are contacted by the tip portion. The instrument is kept in the vicinity of the formed ice mass so that the ice mass is prevented from thawing by having the instrument continuously cool the tissue or is selectively actuated to intermittently cool the tissue so long as the unwanted tissue remains in a frozen state at all times during the procedure.

In one embodiment, the same surgical instrument which is used to disintegrate and break-up the tissue is also used to remove the frozen tissue from the operative site using techniques such as applying a super cooled fluid treatment (irrigation fluid) to the site and then suctioning the fluid and broken-up frozen tissue away from the site. The fluid treatment causes the tissue to be suspended in the fluid and then the fluid and tissue are suctioned away from the site. The instrument may alternatively comprise any number of suitable impacting devices having a rotatable tip or other moving tip for impacting the tissue to cause the tissue to disintegrate and break-up.

In yet another embodiment, multiple surgical instruments are used to disintegrate and remove the tissue. In one embodiment, a cryoprobe is used to cryogenically freeze the unwanted tissue and form the ice mass which encompasses the unwanted tissue and then a second instrument (e.g., a discectomy needle) is applied to the operative site to cut and remove the unwanted frozen tissue from the patient's body. The second instrument typically includes some type of suction means for removal of the unwanted cut tissue. As the tissue is removed, continuous application of the cryoprobe to the operative site ensures that the remaining tissue remains frozen and also permits advancement of the ice mass because more tissue is within the cooling radius of the cryoprobe. This further ensure that all of the unwanted tissue is frozen at all times during the removal procedure.

Advantageously, the present invention finds particular utility in the removal of cancerous tumors and unwanted growths from an organ, gland, or other internal part of the patient's body. Because the unwanted tissue is first cryogenically-treated to form the ice mass encompassing the unwanted tissue, all of the living cells of the cancerous tumor or unwanted growth are frozen and isolated within the ice mass. The ice mass is then preferably maintained in conditions which permit it to remain, frozen (e.g., cryoprobe remains at the operative site) and then completely removed from the patient's body. This eliminates the risk that living cancerous tissue may be disturbed during the isolation and removal process and then spread to another location of the body causing contamination of this other site.

These and other features and advantages of the present invention will be readily apparent from the following detailed description of the invention taken in conjunction with the accompanying drawings, wherein like reference characters represent like elements.

BRIEF DESCRIPTION OF THE DRAWINGS

Other objects, features, and advantages of the invention discussed in the above summary of the invention will be more clearly understood from the following detailed description of the preferred embodiments, which are illustrative only, when taken together with the accompanying drawings in which.

DETAILED DESCRIPTION OF THE PREFERRED EMBODIMENTS

The present invention provides a relatively minimally-invasive surgical approach for removing cancerous or other nondesirable tissue from internal parts of a patient's body. For example, the present surgical approach permits a tumor or other unwanted growth to be removed from an organ, gland, or the like.

According to the present invention, a surgical system and method of use are presented. The surgical system generally includes a cryosurgical instrument for use in freezing the living unwanted tissue by forming an ice mass which completely encompasses the unwanted tissue. The system also includes means for disintegrating or breaking apart the cryogenically-treated tissue and then removing the tissue while the tissue is still in a frozen state. In addition, a monitoring system, using imaging techniques, is preferably used in combination with the cryosurgical instrument and the one or more other surgical instruments that may be used. Suitable monitoring systems include but are not limited to using magnetic resonance imaging, a catscan, a fluoroscope or an ultrasound device.

Figure 1:
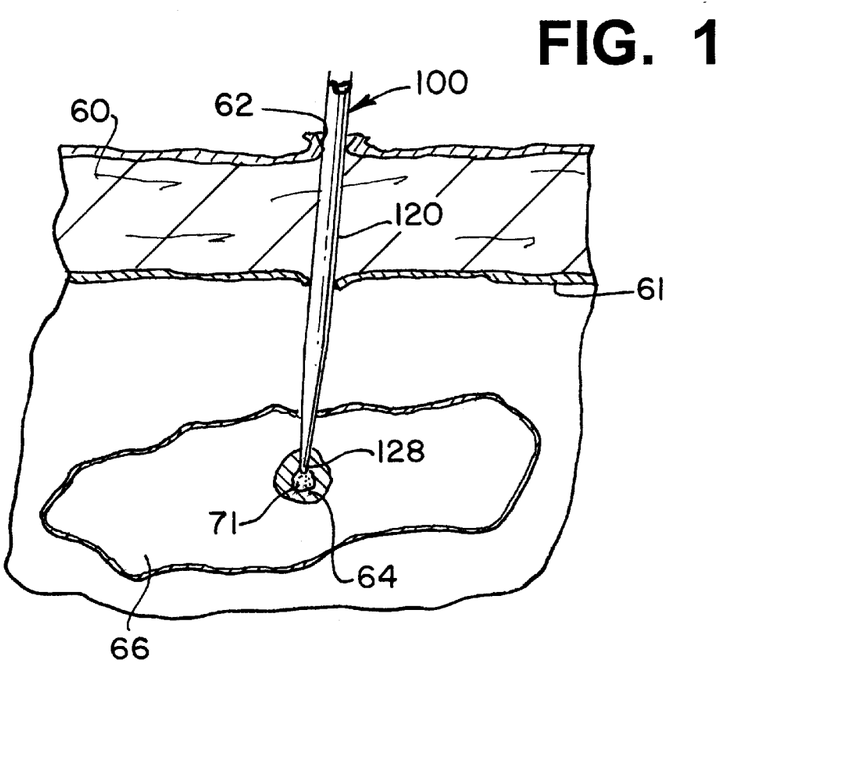
FIG. 1 is an enlarged cross-sectional partial view of a cryosurgical instrument being used to cryogenically treat unwanted tissue contained within an organ, gland or other internal part of a patient's body.
Figure 2:
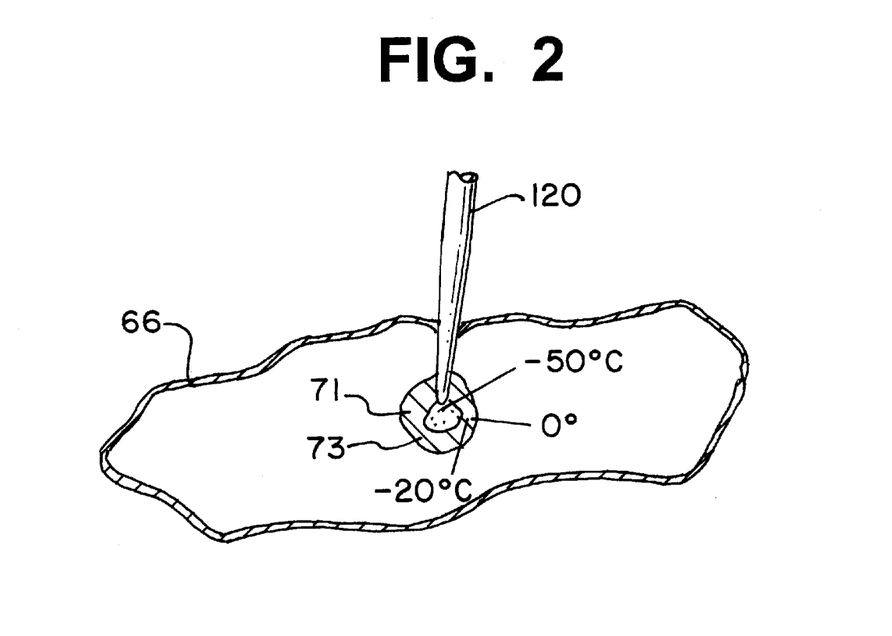
FIG. 2 is an enlarged view of a section a patient's body, including the unwanted tissue, illustrating the formation of an ice mass encompassing the unwanted tissue and also indicating a temperature gradient of the ice mass from the center toward an outer periphery of the ice mass.

The present invention will first be generally described with reference to FIGS. 1 and 2. FIG. 1 illustrates one aspect of the present invention and generally shows a skin layer 60 in which an incision 62 has been made. Prior to making the incision 62, it will be understood that the area to be treated must first be prepared by sterilizing the area. The incision 62 may be made according to any desired surgical procedure. For example, a knife may be used in a known manner to expand and cut tissue from the treatment area. Underneath the skin layer 60, a cohesive mass 64 is formed in an organ or gland, generally and partially indicated at 66. The precise location of the cohesive mass 64 is preferably located using any number of imaging techniques and preferably, the precise location of the cohesive mass 64 is determined by using either a catscan device or a fluoroscope. Thus, the precise location for the formation of the incision 62 will be determined based upon the information received from the imaging techniques.

Organ 66 may comprise any of the organs found in the patient's body, e.g., stomach, liver, and in one exemplary embodiment, the system of the present invention is used to remove unwanted tissue 64 from one or more lungs of the patient. It will be understood that the present invention is likewise effective in removing unwanted tissue 64 from one of the body's glands, e.g., pancreas, using the same or similar procedure as in the case of removing tissue 64 from the organ 66. Also it is within the scope of the present invention that the system disclosed herein may be used to remove unwanted tissue 64 from other remote locations within the person's body or any other location of the body, such as on the skin.

The cohesive mass 64, as opposed to a collection of discrete particles, is typically in the form of a cancerous tumor or other type of unwanted growth. In the exemplary embodiment, the cohesive mass 64 is formed internally within the tissue of the lung so that lung tissue completely surrounds the cohesive mass 64. FIG. 1 also shows a chest wall 61 which is disposed between the organ 66 and the skin layer 60. One of skill in the art will appreciate that other internal body parts and structures, e.g., muscle, etc., are not shown in FIG. 1 but are otherwise disposed between the skin layer 60 and the organ 66. While, the cohesive mass 64 is generally shown as having a round shape, the cohesive mass 64 may have any number of other types of shapes.

According to the present invention, the cohesive mass 64 is cryosurgically treated using a cryosurgical instrument 100. For purposes of simplicity, the cryosurgical instrument 100 will be initially described as being a cryoprobe; however, it is within the scope of the present invention that other types of devices may be used as will become readily apparent from the following description. The cryosurgical instrument 100 is used to freeze the cohesive mass 64 in response to a liquid refrigerant (e.g. nitrogen oxide) flowing within a cryoprobe 120 so that a tip portion 128 thereof reaches and maintains a temperature below the freezing point of the tissue and preferably below about −50° C. (a temperature at which cell destruction results). While the preferred fluid for freezing the tissue is nitrogen oxide, it is understood that other liquid refrigerants capable of generating subfreezing temperatures are available. Nitrogen oxide is a preferred fluid because it is readily available commercially and in many hospital surgical operating rooms and is economical and easy to handle and generates very low temperatures. Nitrogen oxide also is capable of cooling the tip portion 128 to very low temperatures on the order of about −98° C. Other liquid refrigerants suitable for use with the system and method of the present invention are those refrigerants which preferably cool the end tip 128 to temperatures below about −50° C. Examples of such cryogenic liquid refrigerant materials include, for example, liquid nitrogen, freon 14, freon 22, freon 13, liquified air, normally gaseous hydrocarbons, such as propane, carbon dioxide, and isobutane, helium, argon, etc. For purpose of illustration only, the present invention will be described in terms of using nitrogen oxide; however, one will clearly appreciate that other liquid refrigerants may be used and the present invention is not limited to the use of nitrogen oxide. Liquid nitrogen is capable of cooling the end tip 128 to very low temperatures, e.g., about −196° C.; however, because of its physical characteristics at different handling temperatures, a specially constructed insulated cryoprobe 120 is required to permit use of the liquid nitrogen.

Once the incision 62 has been made, the closed end tip 128 of the cryoprobe 120 is inserted into the patient through the incision 62 and maneuvered into place so that the closed end tip 128 contacts an edge of the cohesive mass 64. During actuation of the cryosurgical instrument 100, nitrogen oxide (or another suitable cryogenic fluid) is pumped through the system so that the nitrogen oxide is circulated through the cryoprobe 120, thereby cooling the closed end tip 128 to a temperature below the freezing temperature of tissue. Preferably the closed end tip 128 maintains a temperature of at least below about −50° C. The cryoprobe 120 is designed so that it can be selectively actuated and deactuated by the user.

During operation, the closed end tip 128 of the cryoprobe 120 is brought into contact with or is brought into close proximity with the cohesive mass 64 so as to form an ice mass 71 which fully encompasses the cohesive mass 64 so as to ensure that the entire cohesive mass 64 remains in a frozen state. More specifically, the application of the end tip 128 to tissue produces the ice mass 71 when the end tip 128 is cooled to a sufficiently low predetermined temperature and is held in contact against the tissue for a predetermined amount of time. As one will appreciate, each individual tissue cell is formed largely of liquid (e.g., water) and therefore, when the cell is exposed to temperatures below the freezing point of the liquid for a sufficient period of time, the liquid freezes and expands. This results in the freezing of the tissue and formation of the ice mass 71.

The ice mass 71 is thus formed around the end tip 128 as heat is drawn from the tissue. The ice mass 71 forms around the end tip 128 so that the end tip 128 is located in the central region of the ice mass 71. As one appreciates, the internal body temperature is much higher than the freezing point of water (0° C.) and therefore, the application of the cryoprobe 120 to a discrete limited area of the body serves only to freeze a very small localized area. The freezing effect of the cryoprobe produces a temperature gradient (freezing gradient) within the ice mass 71 itself and therefore, areas farther away from the end tip 128 have higher temperatures. The ice mass 71 itself is defined by a boundary in which the tissue is no longer below 0° C. or another temperature representing the tissue freezing point depending upon the precise application conditions. One exemplary temperature gradient representative of the temperature of different regions of the ice mass 71 is shown in FIG. 2 in which the region immediately surrounding the end tip 128 is cooled to about −50° C. As previously-mentioned and in order to completely destroy cells which are associated with the cohesive mass 64, the end tip 128 is preferably cooled to at least about −50° C. The immediate tissue region will thus be cooled to about −50° C. The ice mass 71 has an outer periphery, generally indicated at 73, which delineates frozen tissue from non-frozen tissue. In other words, this outer periphery defines the extent of the ice mass 71 and also marks the transition where the tissue goes from a temperature of less than about 0° C. to a temperature greater than 0° C. Between the central region of the ice mass 71 around the end tip 128 where the ice mass 71 has its lowest temperature and the outer periphery where the ice mass 71 has its highest temperature, the temperature of the ice mass 71 progressively increases from the central region to the outer periphery. For purpose of illustration only, an intermediate region of the ice mass 71 is indicated as having a temperature of about −20° C. to show that the temperature gradually increases from the central region outward. This is because the freezing effect of the cryoprobe 120 on the tissue decreases as the distance away from the central region increases. Based upon widely understood thermodynamic and other principles, the end tip 128 is capable of only lowering the temperature of tissue immediately surrounding the end tip 128 to a temperature which approximates the end tip 128 temperature. The result is that the ice mass 71, including the cohesive mass 64, has an associated freezing gradient representing that the cohesive mass 64 has different temperature regions across its area.

The extent and the size of the ice mass 71 varies on a number of factors. For example, some of the factors are (1) the tip diameter of the cryoprobe 120; (2) the type of coolant used in the cryoprobe 120 and (3) the flow rate of the coolant into the cryoprobe 120. Because, the ice mass 71 is formed around the end tip 128 of the cryoprobe 120, an increase in the diameter of the end tip 128 results in the ice mass 71 having a larger diameter. Conversely, decreasing the diameter of the end tip 128 results in the ice mass 71 having a lesser diameter. In addition, the type of coolant also varies the size of the ice mass 71. For example, a larger ice mass 71 is achieved when using a liquid coolant that has a very low temperature in comparison with the size of the ice mass 71 that is obtained using a liquid coolant having a much higher temperature. To increase the diameter of the ice mass 71, a liquid coolant having a very low temperature is used, e.g., nitrogen oxide; while a smaller diameter ice mass 71 is formed by using a higher temperature liquid coolant having a temperature of about −50° C. Furthermore, the size of the ice mass 71 may be varied by changing the flow rate of the liquid coolant into the end tip 128. As the flow rate of the liquid coolant is reduced, the heat generated by the patient's body is better able to absorb the cool temperatures of the liquid coolant and therefore, only a small ice mass 71 is formed. In contrast, increasing the flow rate of the liquid coolant results in a greater amount of fresh liquid coolant being in contact with the end tip 128. Thus, the end tip 128 is cooled more efficiently to a lower temperature and this directly results in the surrounding tissue being more effectively cooled. This results in a larger diameter ice mass 71 being formed.

According to the present invention, the formation of the ice mass 71 relative to the cohesive mass 64 is important. The diameter of the ice mass 71 is greater than the diameter of the cohesive mass 64 so as to fully encompass the cohesive mass 64 within the ice mass 71. By tailoring the above-mentioned operating factors, the cryogenic instrument 100 can be tailored to provide an appropriately sized ice mass 71 in view of the size of the cohesive mass 64. It is preferable to have at least about 0.5 cm margin around the entire periphery of the cohesive mass 64 so that diameter of the ice mass 71 will preferably have a diameter of at least 1.0 cm greater than the diameter of the cohesive mass 64. More specifically, the end tip 128 is generally located in the central region of the ice mass 71 as the end tip 128 seats against an outer surface of the cohesive mass 64 and the ice mass 71 forms around the end tip 128. The extent of freezing as measured from the end tip 128 is generally radial in nature so that the ice mass 71 which forms is generally a spherical ice mass 71 with the end tip 128 in the central region thereof. Because a portion of the cohesive mass 64 lies opposite the portion which seats against the end tip 128, the ice mass 71 must be formed so as to extend slightly beyond this opposite portion of the cohesive mass 64. As shown in FIG. 2, the cohesive mass 64 does not have to be centered within the ice mass 71 and often is not. If ice mass 71 becomes too great in size (i.e., excessive marginal tissue around the cohesive mass 64 becomes frozen), the cryoprobe 120 may be selectively deactuated for a period of time to limit the growth of the ice mass 71 so long as the cohesive mass 64 remains in a frozen state at all times.

Because the ice mass 71 includes a freezing gradient, different regions of the cohesive mass 64 will have different temperatures; however, the entire cohesive mass 64 is frozen because it is fully encompassed within the ice mass 71. Preferably, the entire cohesive mass 64 has a temperature of about –50° C. as this is a temperature which will likely cause the total destruction of all tissue cells. However, it will be understood that the entire cohesive mass 64 needs only to be maintained at temperatures which result in the entire cohesive mass 64 being fully frozen. In some applications, portions of the cohesive mass 64 may not be fully destroyed because the temperature of the tissue is not below a selected temperature associated with destruction of the cells; however, the tissue exists in a frozen state by being fully encompassed within the ice mass 71.

According to the present invention, once the cohesive mass 64 is completely encompassed in the ice mass 71, the frozen tissue, including the cohesive mass 64, forming the ice mass 71 is then removed from the patient's body while the tissue remains in a frozen state. This may be accomplished using any number of different types of instruments as will be described in greater detail hereinafter. During removal of the ice mass 71, the tissue forming the ice mass 71 is preferably maintained at freezing temperatures so that the tissue does not thaw. The cryoprobe 120 is kept proximate to the ice mass 71 to ensure that the cohesive mass 64 remains encompassed within the ice mass 71 and the ice mass 71 does not thaw. By maintaining the cohesive mass 64 completely encompassed within the ice mass 71, the frozen tissue may be easily removed from the patient's body and because the ice mass 71 has a greater size than the cohesive mass 64, removal of the ice mass 71 ensures that all of the cohesive mass 64 is removed. This is important because as previously-mentioned, conventional cryogenic treatment simply left the treated cohesive mass 64 within the body for absorption thereof. By removing the cryogenically treated and still frozen cohesive mass 64, the risk that some of the cells of the cohesive mass 64 have not been destroyed and will promote future regrowth is eliminated. The present inventors have thus found that an effective method of removing the cohesive mass 64 is to first encompassed within the cohesive mass 64 in the ice mass 71 and then remove the entire ice mass 71 while it remains in a frozen state.

Figure 3:
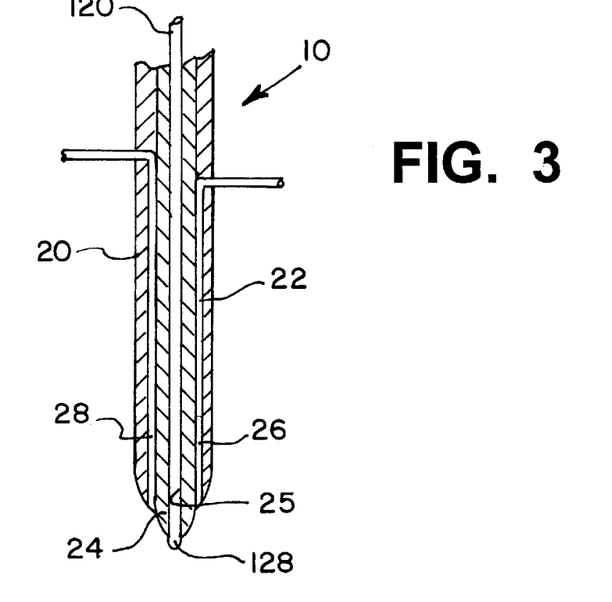
FIG. 3 is an enlarged cross-sectional partial view of a surgical instrument according to one embodiment of the present invention and incorporates the cryosurgical instrument of FIG. 1.

In one embodiment, a single instrument is used for cryogenically treating the cohesive mass 64 and then preparing and removing the frozen tissue. FIG. 3 shows a surgical instrument 10 which is designed to accomplish these operations. In this embodiment, the surgical instrument 10 is used to cryogenically treat and encompass the cohesive mass 64 within the ice mass 71 into smaller frozen pieces and then vibrate or use other motion to disintegrate and break-up the frozen ice mass 71 before removing the ice mass 71 from the patient's body. The surgical instrument 10 includes an elongated probe-like structure 20. The probe 20 may have any number of shapes depending upon the precise application and desires of the user. For purpose of illustration, the exemplary probe 20 has a generally annular cross-section. The probe has an outer casing 22 which is preferably formed of an insulating material.

The instrument 10 includes a vibrating element 24 which is designed to vibrate at a predetermined frequency to cause the break-up (disintegration) of the frozen ice mass 71. The vibrating element is connected to a conventional controller which permits the user to select the operating parameters, e.g., frequency, of the instrument vibrating element 24. The vibrating element 24 resembles a probe with one end extending beyond the outer casing 22 so as to permit the operator to contact the ice mass 71 with this end of the vibrating element 24. The vibrating element 24 has a bore 25 extending therefore for receiving the cryoprobe 120. The vibrating element 24 serves to break apart the frozen ice mass 71 using vibratory or other impacting actions to disintegrate the tissue forming the ice mass 71 before the tissue is removed. In one embodiment, the vibrating element 24 is similar to the vibration generating apparatus disclosed in U.S. Pat. No. 3,589,363, which is hereby incorporated by reference in its entirety. However, any number of suitable methods for vibrating, e.g., ultrasonically or sonically, the element 24 may be used in the practice of the present invention.

Because the bore 25 is open at both ends, the cryoprobe 120 may be disposed within the bore 25 and then directed through the bore 25 so that the end tip 128 of the cryoprobe 120 extends beyond the end of the vibrating element 24. The cryoprobe 120 is thus capable of being retracted and extended within the bore 25 of the vibrating element 24 to permit the user to place the instrument components in desired positions. During the procedure, cryoprobe 120 is preferably left in a location proximate to the cohesive mass 64.

The surgical instrument 10 includes within its outer casing 22, transducer means for converting high frequency electrical energy into mechanical vibrations of high frequency and small amplitude. The requisite high frequency alternating electrical energy may be supplied by a conventional oscillator. To perform the tissue removal according to the present invention, a wide range of frequencies is suitable, for example from 1,000 to 100,000 cycles per second. The surgical instrument 10 will thus preferably include a controller (not shown) for adjusting the frequency and amplitude of the vibrations as well as means for selectively vibrating the probe 20 at desired times. It will be appreciated that other types of devices may be incorporated into the surgical instrument 10 for fragmentation (disintegration) and breaking apart the cryogenically-treated tissue. One type of device that may be used is an impacting device which has a rotatable tip portion for impacting the ice mass 71 to cause disintegration and break-up thereof. The rotating tip portion is generally mechanically actuated and is incorporated into the surgical instrument 10.

The instrument 10 also includes a first fluid carrying member 26 disposed between a portion of the outer casing 22 and the vibrating element 24 and extending to a source of irrigation fluid (not shown). The instrument 10 may include a second fluid carrying member 28 which is disposed between a portion of outer casing 22 and the vibrating element 24 and is connected to a vacuum or the like for aspirating or otherwise removing the super cooled irrigation fluid and piece of broken-up frozen tissue. The first fluid carrying member 26 is designed to carry the super cooled irrigation fluid which has a temperature of below about 0° C. so as not to cause any thawing of the ice mass 71 when the irrigation fluid comes into contact therewith. The first fluid carrying member 24 may have a valve associated therewith for so that the flow of the super cooled irrigation fluid may be momentarily interrupted and suction applied to the operative site by applying a negative pressure within the first fluid carrying member 24. Thus, the first fluid carrying member 24 may be used for both supplying the super cooled irrigation fluid and aspirating the same.

Any number of suitable super cooled irrigation fluids may be used and introduced from the irrigation fluid source to the operative site. One suitable type of cooled irrigation fluid is referred to as a super cooled hypertonic saline solution. A pump (not shown) may be used to pump the irrigation fluid to the operative site. The second fluid carrying member 28 serves to remove the irrigation fluid from the operative site along with broken apart frozen tissue as will be described.

The use of the surgical instrument 10 will now be described with reference to FIGS. 1–3. Once the incision 62 has been made in the skin layer 60, the probe 20 is inserted into the patient through the incision 62 and maneuvered into place so that the probe 20 is proximate to the cohesive mass 64. The cryoprobe 120 is then adjusted within the bore 25 so that the cryoprobe 120 extends sufficiently beyond the vibrating element 24. The end tip 128 of the cryoprobe 120 is placed in contact with one section or edge of the cohesive mass 64. The cryoprobe 120 is then actuated and the end tip 128 cools to a predetermined temperature. Formation of the ice mass 71 results due to the contact between the cryoprobe 120 and the body tissue, including the cohesive mass 64. As explained with reference to FIG. 2, the ice mass 71 is formed so that it completely encompasses the cohesive mass 64. The end tip 128 is formed generally in the center of the ice mass 71. As previously-indicated, there is a general relationship between the ice mass 71 and the diameter of the end tip 128. The diameter of the ice mass 71 which is greater than a diameter of the end tip 128 and is preferably at least two (2) times greater the diameter of the end tip 128. For example, a 3 mm diameter end tip 128 may be used to produce a 7 mm or greater diameter ice mass 71. However, by varying the operating parameters a 3 mm diameter end tip 128 may be used to form a much larger diameter ice mass 71 (e.g., 2 cm).

It will be appreciated that the cryoprobe 120 does not have to be inserted into the bore 25 but may be disposed adjacent to the probe 20 as a different member. In this embodiment, the bore 25 may be used for other purposes such as being connected to a suction source for aspirating the super cooled irrigation fluid which is delivered by the first fluid carrying member 24.

During actuation of the cryoprobe 120, cryogenic fluid is pumped through the cryoprobe 120 so that the fluid cools the end tip 128 to temperatures which produce the ice mass 71 which fully encompasses the cohesive mass 64. Advantageously, the entire cohesive mass 64 does not need to be below about −50° C. (a preferred temperature as it ensures total cell destruction) so long as the entire cohesive mass 64 is frozen. After completely encompassing the cohesive mass 64 within the ice mass 71, the ice mass 71 is removed.

There are several methods of removing the ice mass 71. In one embodiment, the ice mass 71 is continuously cooled by maintaining the cryoprobe 120 in contact with or in close proximity to the cohesive mass 64. The instrument 10 is then actuated so that the vibrating element 24 is activated to cause the ice mass 71 to disintegrate and break apart as a result of being in contact with the vibrating element 24. It will be understood that the vibrating element 24 may be vibrated ultrasonically or sonically or that the vibrating element 24 may be another type of device, such as an impacting device with a rotatable tip. At the same time that the vibrating element 24 is being vibrated and the cryoprobe 120 is being cooled, the super cooled irrigation fluid is delivered to the ice mass 71 so that the super cooled irrigation fluid baths the operative site and causes the broken-up pieces of the frozen ice mass 71 to be suspended in solution. It is important that the super cooled irrigation fluid does not cause thawing of the ice mass 64 because according to the present invention, the tissue forming the ice mass 71, including the cohesive mass 64, is removed while being frozen. The aspiration action of the instrument 10 then causes the super cooled irrigation fluid, including the suspended pieces of the tissue ice mass 71, to be withdrawn from the operative site through the second fluid carrying member 28. Accordingly, this process is continued until all of the cohesive mass 64 is removed from the organ 66. Because the ice mass 71 extends beyond the periphery of the frozen cohesive mass 64, a small amount of frozen tissue surrounding the cohesive mass 64 is likewise removed. This ensures that all of the frozen cohesive mass 64 is removed.

In another embodiment, the cryoprobe 120 may be selectively actuated at the operative site so that the ice mass 71 is continuously maintained at freezing temperatures. If the user determines, using imaging techniques, that the ice mass 71 has become too large is or excessive marginal healthy tissue is being frozen, the user may selectively deactivate the cryoprobe 120 for a short period of time so long as the cohesive mass 64 all remains frozen. The vibrating element 24 is remains actuated to cause the tissue forming the ice mass 71 to break-up while the super cooled irrigation fluid and aspiration component are likewise activated to assist in removing the broken apart pieces of the ice mass 71. As pieces of the tissue ice mass 71 are removed, application of the cryoprobe 120 will cause remaining portions of the tissue ice mass 71 to remain frozen. In other words, the cryoprobe 120 is continuously applied and advanced as frozen tissue is removed. This results in the ice mass 71 being continuously formed and advanced within the operative site. More and more tissue will become frozen as the cryoprobe 120 advances because more and more tissue falls within the radius of freezing as measured from the end tip 128. Advantageously, this also causes more and more tissue to become in closer relationship to the end tip 128 and therefore, this tissue is actually cooled to lower temperatures as its distance to the end tip 128 becomes less. Because the end tip 128 is preferably cooled below −50° C., more and more cells of the tissue, including the cohesive mass 64, are destroyed since they are cooled to at least this temperature. Preferably, the above-mentioned imagining techniques are used so that the removal of tissue and advancement of the ice mass 71 can be monitored and the entire procedure terminated once the surgeon is satisfied that the entire cohesive mass 64 is removed and a sufficient amount of marginal tissue is also removed.

As long as the entire cohesive mass 64 remains frozen, it is not critical whether all of the cells of the cohesive mass 64 have been completely destroyed as the entire frozen cohesive mass 64 is removed from patient's body while in a frozen condition. This is in direct contrast with conventional systems in which it was critical that all of the cells be destroyed because the cohesive mass 64 was left in the body for absorption. The present invention thus offers an improved method which overcomes this limitation. The advancement of the cryoprobe 120 is continued until the entire cohesive mass 64 and some marginal tissue are removed.

It will be understood that the above-mentioned dimensions for the end tip 128, the cohesive mass 64 and the ice mass 71 are merely exemplary and illustrative in nature and do not serve to limit the present invention. The operating parameters, including the diameter of the end tip 128, may be varied accordingly so as to form the ice mass 71 which is of sufficient size to fully encompass the cohesive mass 64. For example, the diameter of the end tip 128 may be about 3 mm and this size may be used to treat tumors having diameters up to 1 cm or even greater. This corresponds into forming an ice mass 71 having a diameter of about 2 cm or slightly greater.

In another embodiment, two or more separate surgical instruments are used. The first instrument is preferably the cryosurgical instrument 100 described previously with reference to FIG. 1. It being understood that the cryosurgical instrument 100 may comprise any number of instruments which are capable of delivering cryogenic fluid to a select, localized area at temperatures below the freezing point of the tissue. One such suitable cryosurgical instrument 100 is set forth in greater detail in U.S. Pat. No. 5,334,181 ('181), which is hereby incorporated by reference in its entirety. The cryosurgical instrument 100 set forth in the '181 patent is essentially a self-contained system for performing cryosurgery, i.e., surgery relying on sub-freezing temperatures to destroy unhealthy or undesired tissues or organs, including in particular, various types of solid benign or malignant tumors.

The cryosurgical instrument 100 of the '181 patent generally includes a mobile manifold which includes the cryoprobe 120 with the manifold being connected to a mobile cart which stores the liquid refrigerant supply and other equipment and control units. The liquid refrigerant is stored in storage dewars (not shown) which may be conveniently stored on the mobile cart. The cryoprobe 120 has an outer casing 122 and a cryogenic fluid channel 124 for delivering and removing the cryogenic fluid from the end tip 128.

Figure 4:
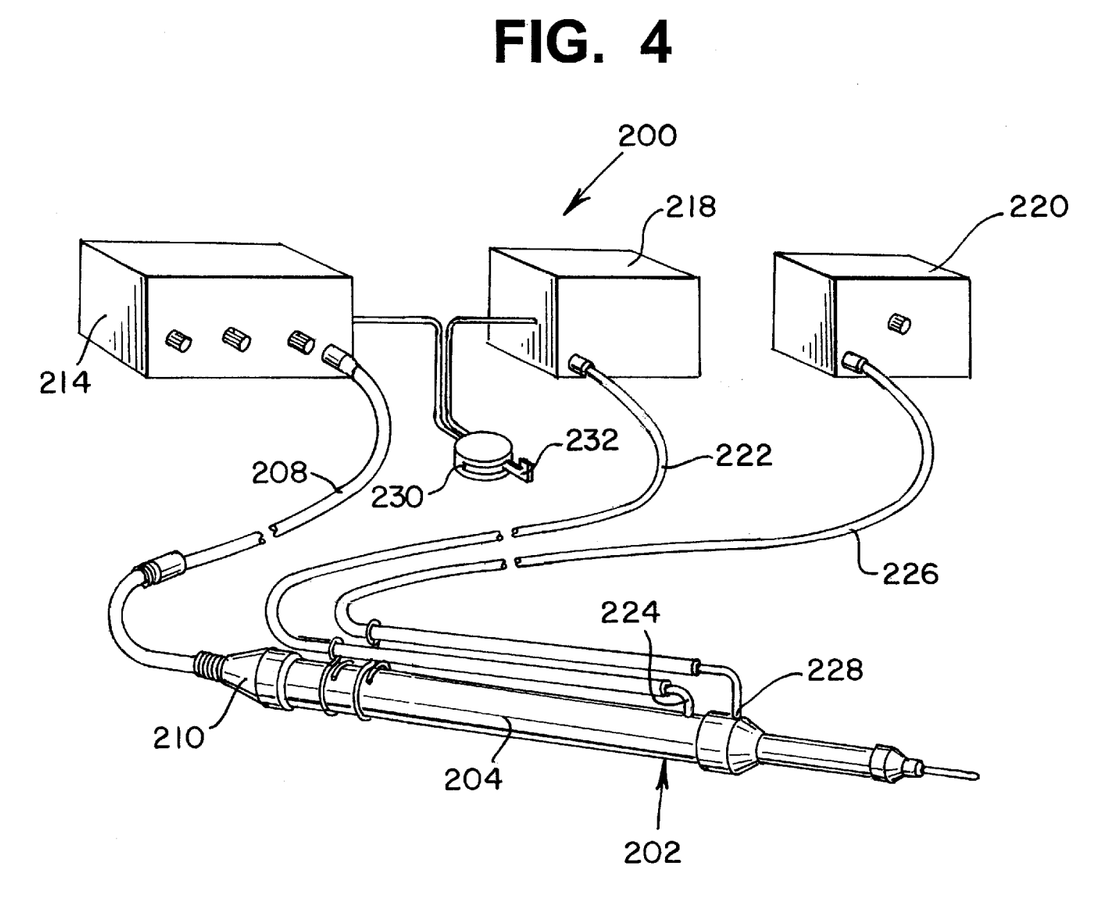
FIG. 4 is a perspective view of one exemplary first instrument for use with the cryosurgical instrument of FIG. 1.

Referring now to FIG. 4 in which a first instrument according to a first embodiment is illustrated and generally indicated at 200. The first instrument 200 comprises an instrument for breaking apart and removing the treated cohesive mass 64 and is generally described in the previously-incorporated U.S. Pat. No. 3,589,363. The first instrument 200 includes a handpiece 202 which is of a size and weight to be comfortably held in a hand of a user and easily manipulated by the user. The handpiece 202 includes within its outer casing 204, transducer means for converting high frequency electrical energy into mechanical vibrations of high frequency and small amplitude. The requisite high frequency alternating current electrical energy is supplied by a conventional oscillator or a piezoelectric crystal included in a first unit 206. Insofar as ability to perform tissue removal is concerned a wide range of frequencies is suitable, for example from 1,000 to 100,000 cycles per second. The first instrument 200 should be vibrated at a frequency and amplitude necessary to disintegrate and break apart the tissue but not liquify the tissue so as to increase the risk of pieces of tissue spreading beyond the operative site location. It may be convenient to select a frequency which is above the range of human hearing, thereby eliminating annoying audible effects obtained at lower frequencies. One exemplary frequency is an ultrasonic frequency of approximately 40,000 cycles per second; however, the first instrument 200 may be used at much lower frequencies, such as 9,000 cycles per second.

The output of the oscillator in the first unit 206 is connected by a pair of leads enclosed within a conduit 208 and coupled through a first end 210 of the handpiece 202 remote from an operative tip 212 thereof. Preferably, the first unit 206 is provided with controls, generally indicated at 214, which allow the user to adjust the frequency and amplitude, whereby the precise frequency of operation may be tuned over a range and the amplitude of electrical signals also may be varied. These controls permit tuning of the first instrument 200 to resonance and adjustment of the vibration amplitude of the operative tip 212 in accordance with the needs of the user.

The first instrument 200 also includes a pump 218, which acts as a means for withdrawing the unwanted material as will be described in greater detail hereinafter, and also a super cooled irrigation fluid supply 220. The pump 218 is coupled to the handpiece 202 via conduit 222 and is operatively connected to the interior of the handpiece 202 through an opening 224 formed in the outer casing 204. The pump 218 is designed to provide a source of suction force for the withdrawal of unwanted particles suspended in the super cooled irrigation fluid and also includes valve means, whereby the conduit 222 may be selectively coupled to the pump 218 or opened to atmospheric pressure.

The super cooled irrigation fluid supply 220 is connected to the handpiece 202 by a conduit 226 and more specifically, the conduit 226 accesses the interior of the handpiece 202 through an opening 228 formed in the outer casing 204. The super cooled irrigation fluid supply 220 may include a reservoir of a premixed solution of appropriate type and a suitable pump, or mixing means whereby the required solution is prepared on a continuous basis. The handpiece 202 includes internal fluid passages (not shown) coupled to the conduits 222, 226, whereby, at the operative tip 212, there may be provided both a flow of super cooled irrigation fluid and a withdrawal of unwanted particles suspended in the super cooled irrigation fluid.

A switch 230 is preferably provided to enable control of the oscillator (first unit 206) and pump 218 during manipulation of the handpiece 202 by the user. Any number of switches 230 may be used and in one exemplary embodiment, the switch 230 is of a type which rests on the floor and includes a control lever 232 adapted to be actuated by a foot so that a number of setting may be achieved. The switch 230 is coupled to the first unit 206 and the pump 218 via conductors 234 to control the components thereof.

Figure 5:
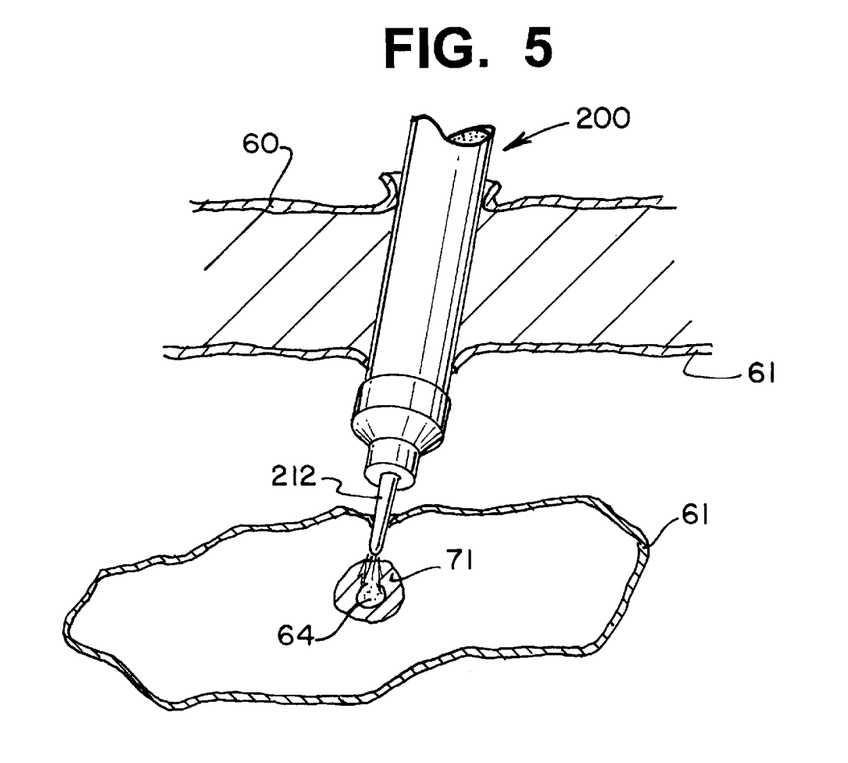
FIG. 5 is an enlarged perspective and cross-sectional partial view of the first instrument of FIG. 4 shown in use according to the method of the present invention.

An exemplary surgical approach using two instruments according to the present invention will now be described with reference to FIGS. 4 through 5. For purpose of illustration only, one surgical method according to the present invention will be described with reference to the first instrument 200 of FIG. 3. After the unwanted tissue 64 has been first cryogenically frozen and encompassed within the ice mass 71, the first instrument 200 is inserted into the incision 62 that has previously been formed for reception of the cryosurgical instrument 100 or the incision 62 is modified so that the surgical system of the present invention may be used while the cryoprobe 120 remains disposed at the operative site. The incision 62 is formed and/or modified preferably subsequent to the local area being prepared by sterilization. Once the size of the incision 62 is proper, the tip portion 212 of the ultrasonic probe (first instrument 200) is inserted into the patient. Because the operative site has been previously imaged using known procedures, the tip portion 212 is then manipulated so that the tip portion 212 contacts the complete operative site (e.g., the ice mass 71 encompassing the cohesive mass 64) which has been cryogenically-treated previously. The use of the ultrasonic probe 200 is continued until all of the tissue at the operative site has been disintegrated due to the vibratory action of the tip portion 212. It will be appreciated that the ultrasonic probe 200 contacts tissue which forms the ice mass 71. In this embodiment as with the previous embodiment, it is important that the cohesive mass 64 remain frozen during the procedure and therefore, the cryoprobe 120 (not shown) is maintained in its position at the operative site to ensure that the ice mass 71 does not thaw during the removal process. Also as removal of cohesive mass 64 occurs, the cryoprobe 120 advances causing advancement of the ice mass 71 as previously-mentioned.

Furthermore, the use of the ultrasonic probe 200 also includes the previously-described irrigation and aspiration processes. The super cooled irrigation fluid is delivered to the tip portion 212 to bath the disintegrated tissue with a fluid causing the broken-up pieces of the tissue to be suspended in the super cooled irrigation fluid. Suction is then applied to the operative site, specifically to the tip portion 212, to cause the super cooled irrigation fluid and suspended pieces of tissue to be aspirated from the operative site. This results in the effective removal of the frozen cohesive mass 64 without pieces of the cohesive mass 64 being spread from the operative site to other parts of the body. In addition, tissue surrounding the cohesive mass 64 will be removed during the use of the ultrasonic probe 200, as previously discussed. It will be understood that the surgeon may further cryogenically treating the surgical area after the first instrument 200 has been used to remove the cohesive mass 64. For example, the surgeon may feel that it is necessary to use the cryoprobe 120 on the tissue that remains at the surgical site after use of the first instrument 200 because the surgeon wants to make sure that all of the cohesive mass 64 has been removed. Thus, the surgeon may treat substantially all of the cohesive mass 64, remove the treated mass 64 and then cryogenically treat a small area from which the cohesive mass 64 was removed so that a predetermined amount of marginal tissue around the cohesive mass 64 is removed to ensure that all of the tumorous cells have been removed.

In another embodiment of the present invention, several instruments may be used to disintegrate and remove the cohesive mass 64. In this other embodiment, the first instrument used is a cryosurgical instrument, such as cryoprobe 120 illustrated in FIG. 1. This instrument is used to freeze tissue and form the ice mass 71 which encompasses the cohesive mass 64. As mentioned hereinbefore, the cryoprobe 120 is continuously positioned at the operative site so that the ice mass 71 remains formed and the entire cohesive mass 64 always remains in the frozen state.

Figure 7:
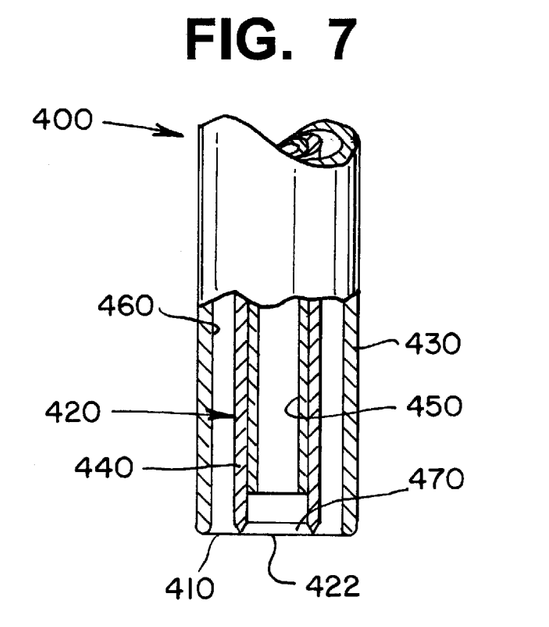
FIG. 7 is an enlarged cross-sectional partial view of a second instrument for use with the cryosurgical instrument of FIG. 1 for the cutting and removal of frozen unwanted tissue.

Referring now to FIG. 7, once the frozen cohesive mass 64 to be treated has been disintegrated by the cryosurgical instrument 100 (FIG. 1), a second instrument 400 is inserted through the incision. According to this embodiment, the second instrument 400 comprises a cutting and suctioning instrument, such as a Nucleotome® needle (probe) manufactured by Surgical Dynamics. The second instrument 400 has a distal tip 410 opposite to a handpiece (not shown) which is designed to be gripped by the user. The second instrument 400 also preferably has a hollow needle 420 with a hollow distal tip 422 having a predetermined suitable width. For example, the distal tip 422 may have a width of approximately 2, 2.5, 3.2, 3.5, or 4.7 mm.

The needle 420 preferably includes an outer member 430 and an inner member 440. In the exemplary embodiment illustrated, the outer and inner members 430, 440 have a generally annular cross section and thus comprise generally concentric tubular structures. The inner member 440 terminates in a cutting implement, such as a guillotine-like cutting blade, generally indicated at 470. A vacuum is applied within a lumen 450 disposed within the inner member 440 to provide suction at the distal end 422. Additionally, a stream of cooled irrigation fluid, is passed through an annular passage lumen 460 between the outer and inner members 430, 440 of the second instrument 400. The cooled irrigation fluid flushes the treatment site and also causes the cut tissue to be directed into the hollow distal tip 422 of the second instrument 400 and suctioned by the vacuum within the lumen 450.

The inner member 440 is longitudinally, i.e., axially, movable with respect to the outer member 430, and either may be intermittently regularly moved back and forth, or may be moved at predetermined intervals controlled by the user (surgeon). When the inner member 440 moves toward the distal tip 410 of the second instrument 400, the cutting implement 470 cuts a part of the frozen cohesive mass 64, that has been suctioned into the hollow distal end region from the remaining tissue portion. This tissue is cut, with a guillotine-like action, from the remaining portion of the frozen tissue. The frozen cut portion is suctioned, by the vacuum applied within the lumen 450, along with the super cooled irrigation fluid, to a collection vessel. It will be appreciated that the use of a separate instrument, namely the second instrument 400, for cutting the frozen tissue may be necessary or desired when removing certain types of frozen tissue in certain locations of the body.

The above steps of severing, suctioning, and removing the ice mass 71 are repeated while preferably maintaining the cohesive mass 64 at freezing temperatures until all of the unwanted tissue is removed. A monitoring system is preferably used to continuously monitor the progress and success of the present surgical procedures.

Figure 6:
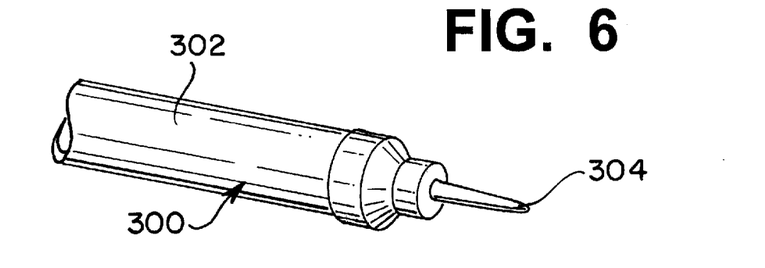
FIG. 6 is a perspective view of one exemplary first instrument for use with the cryosurgical instrument of FIG. 1.

Referring now to FIG. 6 in which another first instrument for use with the cryosurgical instrument 100 is illustrated and generally indicated at 300. In this embodiment, the first instrument 300 includes a handpiece 302 to be comfortably held in the hand of the user. The first instrument 300 also includes a tip portion 304 which is designed to contact and treat the cryogenically-treated tissue. The tip portion 304 either comprises a mechanically rotatable tip which is designed to impact and cause the disintegration and break-up of the unwanted tissue. In yet another embodiment, the first instrument may be a suitable laser device which directs a laser beam at the ice mass 71 to cause a small section thereof to vaporize. Because the laser only vaporizes a very small tissue area of the ice mass 71, the heat given off by the laser is not significant enough to cause the ice mass 71 to thaw to a degree that would cause the ice mass 71 to unfreeze.

In yet another aspect of the present invention, a therapeutic agent is introduced into the operative site after the surgeon has effectively removed all of the cohesive mass 64. Any number of known therapeutic agents may be introduced using any one of the surgical instruments described herein and the therapeutic agent may be in a liquid, solid, or gas state or a combination thereof. The therapeutic agent is generally a medicinal agent that enhances the effects and benefits of chemotherapy treatment or otherwise enhances the destruction of the unwanted tissue (tumor). One type of therapeutic agent is a chemotherapeutic agent designed to increase the effectiveness of the basic chemotherapy treatment. The therapeutic agent may be introduced in one of the fluid carrying members of the probe 20 so that the therapeutic agent is delivered through the end tip 24 such that the agent contacts the organ 66 at the location where the cohesive mass 64 has just been previously removed. These type of agents are designed to further treat the tissue at the operative site so as to reduce the likelihood that the cohesive mass 64 will return. The surgical instrument 10 is then removed from the patient and the incision 62 is closed.

It will be appreciated that the therapeutic agent may also be delivered to the operative site during the surgical procedure itself. For example, the therapeutic agent may be delivered to the operative site during the disintegration process in which the cryogenically-treated tissue is disintegrated and broken-up. The therapeutic agent treatment may thus be done simultaneously with the disintegration process. The therapeutic agent treatment may occur at other times during the complete surgical procedure. Once again, the introduction of the therapeutic agent must not cause the ice mass 71 to thaw because it is important that the cohesive mass 64 remain completely frozen as it is removed from the patient's body.

In another aspect of the present invention, a known tissue dye may be used. As is know, some types of tissue, including tumors, absorbs certain dyes to permit visual identification of the tissue that has absorbed the dye. Certain medical equipment may be used to easily visually identify that tissue that has absorbed the dye. Thus, if a dye is used which is absorbed only by the cohesive mass 64 and not the healthy tissue surrounding the cohesive mass 64, the cohesive mass 64 will be easily identifiable. Thus, when the ice mass 71 is formed it will actually be formed of normal color ice (white/clear) and dyed ice which represents the frozen cohesive mass 64. Using an endoscope or other medical device, the user can continuously monitor the cohesive mass 64 in terms of its position and how much of the cohesive mass 64 remains during the procedure. This makes removal of the cohesive mass 64 easier as it will be more apparent to the user when all of the cohesive mass 64 is removed.

In yet another aspect of the present invention, a sclerosing agent or heat application is used to cauterize any blood vessels that may have opened at the operative site during the entire surgical procedure. The sclerosing agent may be introduced using conventional techniques once the cohesive mass 64 is completely removed.

Figure 8:
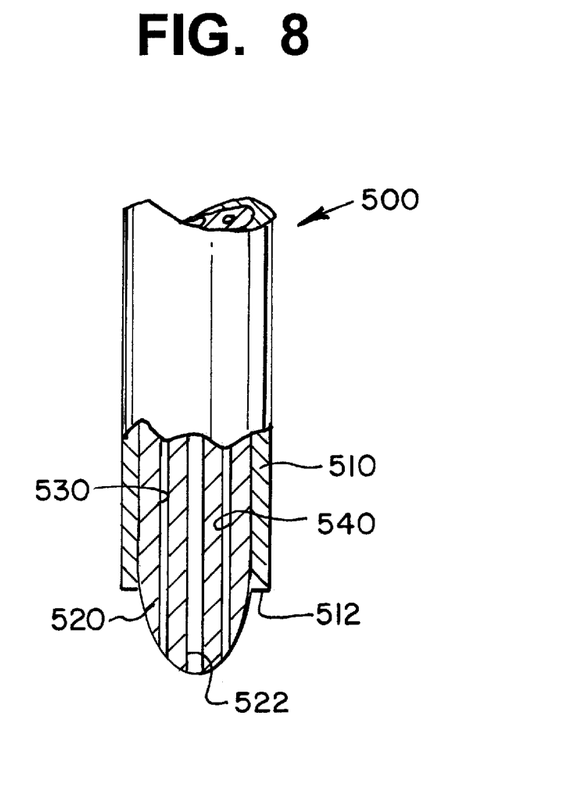
FIG. 8 is an enlarged cross-sectional partial view of a surgical instrument according to another embodiment of the present invention for both cryosurgically freezing unwanted tissue and removal thereof while the unwanted tissue remains in the frozen state.

Now referring to FIG. 8, another single instrument 500 is illustrated. The instrument 500 includes a cryosurgical component 510 and a vibrating element 520. The cryosurgical component 510 may comprise a cryoprobe as disclosed with reference to FIG. 1 or may comprise any other type of cryosurgical instrument that is capable of cooling tissue to cryogenic temperatures. In this embodiment, the cryosurgical component 510 is in the form of an annular sleeve member with a bore extending through a central portion thereof. The bore receives the vibrating element 520 in a displaceable manner so that the vibrating element 520 may be axially moved within the bore. This permits the vibrating element 520 to be extended beyond an end tip 512 of the cryosurgical component 510 or retracted therefrom.

The vibrating element 520 may comprise the same type of instrument described in reference to FIG. 3 and generally is connected to a controller that permits the user to selectively. vibrate the element 520 at a predetermined frequency, etc. The vibrating element 520 may be either ultrasonically or sonically vibrated and causes the disintegration and break-up of the ice mass 71 (FIG. 1) when vibrating element 520 contacts the ice mass 71. The vibrating element 520 includes a bore 522 which may perform one or more functions. For example, the super cooled irrigation fluid may be introduced through the bore 522 and/or the bore 522 may be connected to a suction source for aspirating the broken apart pieces of the tissue ice mass 71 and the super cooled irrigation fluid.

The vibrating element 520 may also include a first fluid carrying member 530 and/or a second fluid carrying member 540. These members 530, 540 may perform the same functions as the equivalent members discussed with reference to FIG. 3. Thus, the members 530, 540 may be used to perform the functions of delivering the super cooled irrigation fluid to the operative site and then aspirating the broken apart pieces of tissue and super cooled irrigation fluid.

It is understood that the precise structures of the surgical instruments described herein are merely exemplary in nature and do not serve to limit the scope of the present invention. The instruments may have any number of configurations so long as the instrument has a cryogenic element for delivering cryogenic fluid for cooling of the end tip to form the ice mass encompassing the cohesive mass and also includes components for disintegrating the frozen tissue forming the ice mass before removing it from the body in a frozen condition.

Accordingly, the present invention permits an alternative and effective technique for the removal of unwanted tissue from a site underneath the skin layer of the patient. The present invention finds particular utility in the removal of cancerous tumors and unwanted growths from an organ or gland of the patient's body. Because the unwanted tissue is first cryogenically-treated using a cryosurgical system, the living cancerous or tumorous cells are first encompassed within ice mass 61 so as to isolate the frozen unwanted tissue and permit its removed using various techniques. By removing the unwanted tissue while it is remains in a frozen state, the system and method of the present invention eliminate the risk that living cancerous tissue may be disturbed during the isolation and removal process and then spread to another location of the body. The present invention thus eliminates the associated disadvantages of conventional cryosurgical techniques which left the treated tissue within the body for absorption. The present invention also provides a relatively minimally-invasive surgical approach for treating and removing cancerous tissue or other unwanted growths from within the body. The present invention also provides an alternative method of introducing a chemotherapeutic agent to a post-operative site.

It is also within the scope of the present invention that the surgical approach described herein may be used to treat and remove tissue from other locations of the body, such as on a portion of the skin itself. Furthermore, the present surgical approach is not limited to application on a human but rather it is expected that the present invention may be used to remove unwanted tissue from animals and the like.

While the foregoing description and drawings represent the preferred embodiments of the present invention, it will be understood that various additions, modifications, and substitutions may be made without departing from the scope of the present invention as defined in the accompanying claims. In particular, it will be clear that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportion, materials, and components and otherwise, used in the practice of the present invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A surgical instrument for freezing and removing a mass of unwanted tissue from a patient's body, the surgical instrument comprising:
   an outer casing;
   an element having a distal section disposed between the outer casing, the element being coupled to a control system for causing movement of at least the distal section of the element, the element having a bore extending therethrough; and
   a cryoprobe received within the bore such that the cryoprobe is displaceable between an extended position where the cryoprobe extends beyond a distal end of the element and a retracted position where the cryoprobe is retracted within the bore, the cryoprobe for cooling the mass of unwanted tissue at a temperature sufficiently below the freezing point of the tissue and for a predetermined time period to form an ice mass which encompasses the mass of unwanted tissue and wherein upon activation, the element transfers energy to the ice mass to cause an interior of the ice mass that contains the cryosurgically treated unwanted tissue to break apart into smaller tissue pieces.

2. The surgical instrument of claim 1, wherein the outer casing is coupled to transducer means for vibrating the outer casing at a prescribed frequency.

3. The surgical instrument of claim 1, wherein the distal section of the element extends beyond a distal end of the outer casing.

4. The surgical instrument of claim 1, wherein the element is a vibrating element which ultrasonically vibrates at a prescribed frequency.

5. The surgical instrument of claim 1, wherein the element has a distal tip that is rotatable for impacting the ice mass to cause the ice mass to break into the smaller tissue pieces.

6. The surgical instrument of claim 1, wherein the cryoprobe has a tip end which is cooled with a refrigerant to a temperature below about −50° C.

7. The surgical instrument of claim 1, further including: a first fluid carrying channel formed between the outer casing and the element for delivering a super cooled irrigation fluid so as to cause the smaller tissue pieces to become suspended in the super cooled irrigation fluid.

8. The surgical instrument of claim 7, further including a second channel formed between the outer casing and the element for aspirating the super cooled irrigation fluid and the smaller tissue pieces.

9. The surgical instrument of claim 7, wherein the first fluid carrying channel has a valve associated therewith so that the flow of the super cooled irrigation fluid can be selectively interrupted and negative pressure can be applied to the first fluid carrying channel to cause aspiration of the super cooled irrigation fluid and the smaller tissue pieces.

10. A surgical instrument for freezing and removing a mass of unwanted tissue from a patient's body, the surgical instrument comprising:
    a cryosurgical component in the form of an outer sleeve having a bore formed therein, the cryosurgical component cooling the mass of unwanted tissue at a temperature sufficiently below the freezing point of the tissue and for a predetermined time period to form an ice mass which encompasses the mass of unwanted tissue;
    an element received within the bore such that it is displaceable between an extended position where a distal tip thereof extends beyond a distal end of the cryosurgical component and a retracted position where the element is retracted within the bore, the element being coupled to a control system for causing selective movement of the element to cause an interior of the ice mass that contains the cryosurgically treated unwanted tissue to break apart into smaller tissue pieces.

11. The surgical instrument of claim 10, wherein the cryosurgical component comprises a cryoprobe in the form of an annular sleeve and the element comprises an annular vibrating probe.

12. The surgical instrument of claim 10, wherein the element has a first fluid carrying channel formed therein which is open at the distal tip of the element to permit a super cooled irrigation fluid to be delivered to the site where the ice mass is being broken into smaller tissue pieces.

13. The surgical instrument of claim 10, wherein the element has a second fluid carrying channel formed therein which is open at the distal tip of the element, the second fluid carrying member being coupled to a suction source for aspirating the smaller tissue pieces.

14. The surgical instrument of claim 10, wherein the element moves axially within the bore.

15. The surgical instrument of claim 10, wherein the cryosurgical component comprises an annular sleeve and the element comprises an annular probe that is received within the bore, the distal tip of the element having at least one open channel.

16. The surgical instrument of claim 10, wherein the element oscillates at a prescribed frequency and upon contact with the ice mass, the oscillating distal tip causes the ice mass to break into smaller pieces.

17. The surgical instrument of claim 10, wherein an outer surface of the element seats an inner surface of the cryosurgical component, the inner surface defining the bore.

18. The surgical instrument of claim 10, wherein the element includes a central bore formed therein, a first fluid carrying channel formed therein such that it is open at the distal tip of the element, and a second fluid carrying channel formed therein such that it is open at the distal tip of the element, the first and second fluid carrying channels being formed between the central bore and an outer peripheral edge of the element.

19. The surgical instrument of claim 18, wherein the central bore is in communication with a source of super cooled irrigation fluid which is delivered through the central bore to an operative site.

20. The surgical instrument of claim 18, wherein the first fluid carrying channel is operatively coupled to a suction source for aspirating the smaller tissue pieces from an operative site.

21. The surgical instrument of claim 18, wherein the second fluid carrying channel performs the same function as the first fluid carrying channel.

22. A surgical instrument for freezing and removing a mass of unwanted tissue from a patient's body, the surgical instrument comprising:

a cryosurgical component in the form of an outer sleeve having a bore formed therein, the cryosurgical component cooling the mass of unwanted tissue at a temperature sufficiently below the freezing point of the tissue and for a predetermined time period to form an ice mass which encompasses the mass of unwanted tissue;

a probe received within the bore such that it is displaceable between an extended position where a distal tip thereof extends beyond a distal end of the cryosurgical component and a retracted position where the probe is retracted within the bore, the probe being coupled to a control system for causing the probe to mechanically vibrate to cause an interior of the ice mass that contains the cryosurgically treated unwanted tissue to break apart into smaller tissue pieces when the distal tip contacts the ice mass, wherein the probe contains a first feature for ensuring that the smaller tissue pieces remain in a frozen state and a second feature for aspirating the frozen tissue pieces.

23. The surgical instrument of claim 22, wherein the first feature is a first fluid carrying channel formed in the probe and in communication with a source of super cooled irrigation fluid so that the super cooled irrigation fluid is delivered to an operative site to ensure that the smaller tissue pieces remain frozen.

24. The surgical instrument of claim 23, wherein the second feature is a second fluid carrying channel formed in the probe and in communication with a suction source for aspirating the smaller tissues pieces along with the super cooled irrigation fluid.

25. A method of freezing and removing a mass of unwanted tissue, the method comprising:

cryosurgically cooling the mass of unwanted tissue to a temperature at least below a freezing point of the tissue and for a predetermined period of time so that an ice mass forms and encompasses the unwanted tissue;

treating an interior of the ice mass that contains the cryosurgically treated unwanted tissue to reduce the cryosurgically treated unwanted tissue into smaller frozen tissue pieces;

bathing the frozen tissue pieces with a super cooled irrigation fluid to form a suspension of frozen tissue pieces within the irrigation fluid; and withdrawing the resultant suspension of frozen tissue pieces along with the irrigation fluid.

26. A method as in claim 25, wherein the cooling of the tissue comprises cooling a tip of a cyrosurgical instrument to a temperature at which destruction of cells is achieved.

27. A method as in claim 25, wherein the mass of unwanted tissue comprises a tumor formed in one of an organ and a gland.

28. A method as in claim 25, wherein the ice mass has a diameter at least twice as great as a diameter of the unwanted tissue.

29. A method as in claim 25, wherein cryosurgically cooling the mass comprises:

selecting a tip diameter in view of a diameter of the mass of unwanted tissue;

selecting a cryogenic fluid; and controlling a fluid flow rate of the cryogenic fluid so as to form the ice mass of sufficient size so that it encompasses the unwanted tissue.

30. A method as in claim 25, wherein treating the ice mass comprises:

impacting and rotating a tip portion of a rotating impacting device to cause the ice mass to break-up.

31. A method as in claim 25, wherein treating the ice mass comprises:

vibrating the ice mass to emulsify the ice mass.

32. A method as in claim 25, wherein the ice mass comprises a substantially spherical ice ball.

33. A method as in claim 25, further including:

introducing a tissue dye to cause the mass of unwanted tissue to change color and become identifiable relative to marginal tissue surrounding the mass of unwanted tissue.

34. A method as in claim 25, further including:

introducing a sclerosis agent once the mass of unwanted tissue has been removed, the sclerosis agent for cauterizing any blood vessels that may have opened during the removal of the mass of unwanted tissue.

35. A method as in claim 25, wherein cryogenically treating the mass of unwanted tissue comprises:

cooling the entire mass of unwanted tissue to a temperature below about −50° C.

36. A method as in claim 25, wherein removing the broken-up tissue comprises:

using an instrument to cut the frozen ice mass into smaller frozen pieces which are removed.

37. A method as in claim 32, wherein a remaining portion of the ice mass including the unwanted tissue is continuously cryogenically treated so as to prevent thawing of the ice mass during the removal of the tissue.

* * * * *